United States Patent [19]

Metzler

[11] Patent Number: 4,521,188
[45] Date of Patent: Jun. 4, 1985

[54] DOWEL PIN FOR DENTAL MODELS

[75] Inventor: Steven Metzler, Cherry Hill, N.J.

[73] Assignee: National Keystone Products Co., Philadelphia, Pa.

[21] Appl. No.: 542,175

[22] Filed: Oct. 14, 1983

[51] Int. Cl.³ .............................. A61C 19/00
[52] U.S. Cl. .................................... 433/74
[58] Field of Search ................... 433/74, 220, 221

[56] References Cited

U.S. PATENT DOCUMENTS

| 3,153,283 | 10/1964 | Weissman | 433/74 |
|---|---|---|---|
| 3,226,827 | 1/1966 | Spalten | 433/74 |
| 3,277,576 | 10/1966 | Kraft | 433/74 |
| 3,478,428 | 11/1969 | Stengel | 433/74 |
| 3,552,018 | 1/1971 | Zahn | 433/74 |
| 3,871,804 | 3/1975 | Cooper | 425/175 |
| 3,885,313 | 5/1975 | Kikuchi et al. | 433/74 |
| 3,969,820 | 7/1976 | Kulig et al. | 433/74 |
| 4,054,995 | 10/1977 | Yoshida | 433/74 |
| 4,122,606 | 10/1978 | Roman | 433/74 |
| 4,238,189 | 12/1980 | Tirino | 433/74 |
| 4,240,605 | 12/1980 | Waltke | 249/54 |
| 4,242,812 | 1/1981 | Randoll et al. | 434/263 |
| 4,265,619 | 5/1981 | Lucki et al. | 433/74 |

FOREIGN PATENT DOCUMENTS 1088188 2/1957 Fed. Rep. of Germany ........ 433/74

Primary Examiner—John J. Wilson
Attorney, Agent, or Firm—Robert C. Podwil

[57] ABSTRACT

A dowel pin has a plurality of facets which provide numerous planes, edges and angles to constrain the dowel pin and an associated die segment to a particular orientation with respect to the base of a dental model, and to enhance the durability of the model.

4 Claims, 7 Drawing Figures

U.S. Patent   Jun. 4, 1985   4,521,188
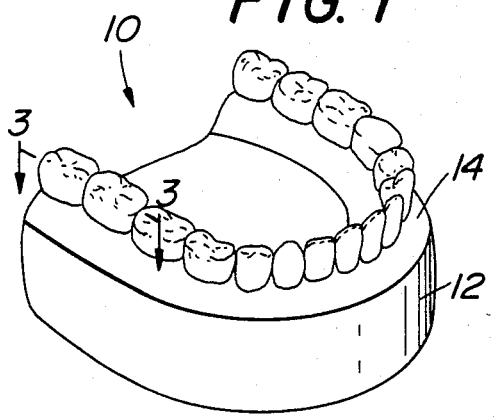
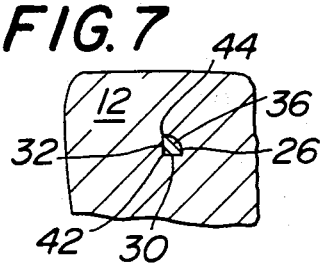
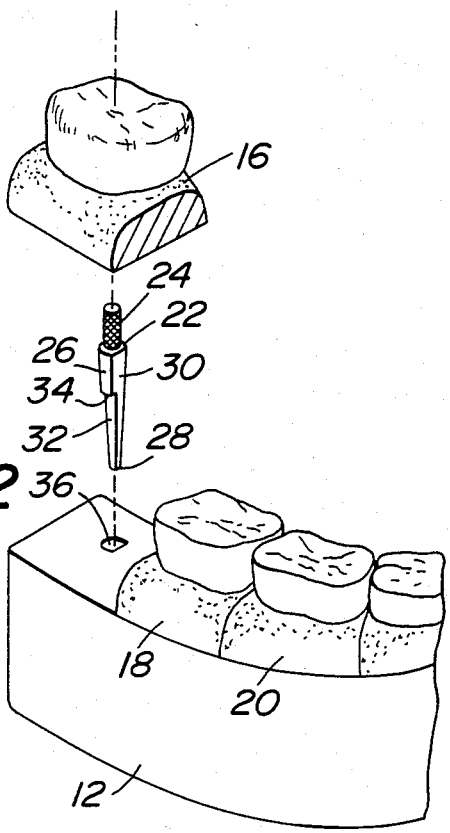
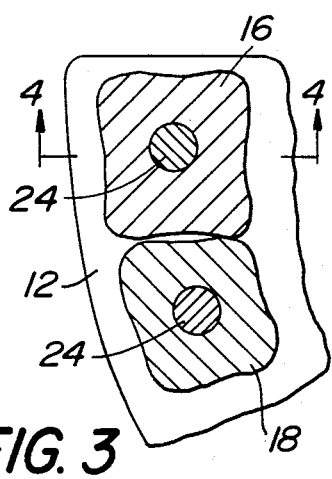
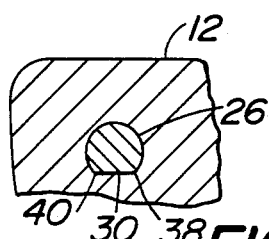
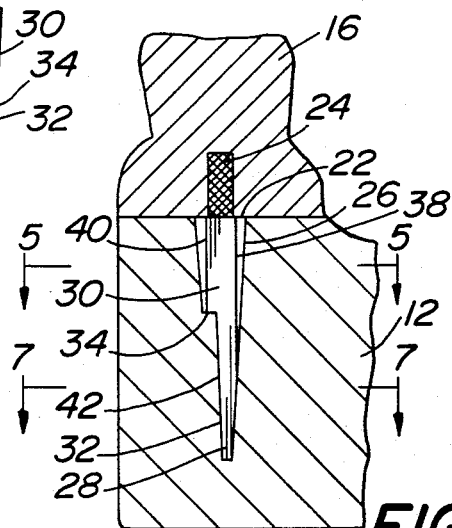

DOWEL PIN FOR DENTAL MODELS

BACKGROUND OF THE INVENTION

This invention relates to dowel pins for dental models, and more particularly, to a dowel pin suitable for use in dental models which have removable dies.

In the making of dental crowns or bridge work, a starting point for the work of a dentist or dental technician is often a replica, accurate in shape and size, of the actual dentition of the patient. As was explained in U.S. Pat. No. 4,054,995, to Yoshida issued Oct. 25, 1977, and elsewhere, such replicas, referred to in dental terminology as "models", may be made by taking an impression of the patient's teeth and gums which provides a "negative" model of the patient's dentition. From the "negative", a "positive" can be cast in dental stone or plastic, and the positive forms the model from which a dental prosthesis may be prepared.

Typically, models are cast in a single piece, and then cut into segments encompassing perhaps one or two teeth, thereby to facilitate separation of the individual segments from the overall model for close study and individual use.

It is important that provision be made to precisely and positively relocate each segment with respect to the model when desired. For this purpose, various techniques and apparatus have been proposed. In one conventional and widely used system, tapered dowel pins are embedded in the model before molding of a base. After hardening of the base, the model can be removed from the base and cut into segments. The segments may thus be removed individually from the base, and returned to the base by insertion of the pins into the openings in the base cast.

In systems which have heretofore been proposed, numerous suggestions have been made for means to insure precise relocation of the dowel pins, and hence the die segments, with respect to the base. For example, in one system, tapered pins having a flat facet or V-shaped groove are used. In another, specially made pins which are rectangular or oval in cross-section are used. Such pins serve to "key" or orient the lingual, labial or buccal aspects, as the case may be, of the die segments to the desired orientation. Other pin systems, such as the one described in the above-mentioned U.S. Pat. No. 4,054,995, utilize sleeves or sockets embedded in the base, to receive and orient the ends of the pins. Other systems, such as the one illustrated in U.S. Pat. No. 3,937,773, to Huffman, issued Feb. 10, 1976, use a plurality of pins to establish the desired orientation of the die segment, while others, such as the one illustrated in U.S. Pat. No. 3,875,665, to Weissman, issued Apr. 8, 1975, employ pins which, in a unitary structure, provide in effect multiple pins.

It is an object of the present invention to provide a novel dowel pin for use in dental models which has all of the advantages of conventional single dowel pins, but which facilitates the removal from the model and the precise return of individual die segments.

It is a further object of this invention to provide a dowel pin which may be used in dental models without the need for cooperating parts such as sleeves, sockets or the like associated with the base, and still a further object to provide a dowel pin the use of which results in a durable and accurate model.

Other objects will appear hereinafter.

SUMMARY OF THE INVENTION

The foregoing and other objects are realized, in a presently preferred form of the invention, by providing a dowel pin made of brass or other suitable material of the conventional kind, and having a stem which may be embedded in and affixed to a die segment. The preferred form of dowel pin also includes a body portion coupled to the stem, and having a tapered, generally frusto-conical shape. The body portion has a first facet facing laterally outwardly with respect to the longitudinal axis of the body portion, a second facet, also facing laterally outwardly, and a third facet, extending transversely with respect to the axis of the body portion and facing the narrowed, distal end of the body portion. Thus configured, the dowel pin cooperates with a recess in the base to accurately orient the die segment with respect to the base.

In the presently preferred form of the apparatus, the third facet is disposed in the upper half of the body portion, and preferably at a location approximately two-thirds of the axial dimension of the body portion from the distal end.

There are seen in the drawings forms of the invention which are presently preferred, it being understood that this invention is not limited to the precise arrangements and instrumentalities shown.

BRIEF DESCRIPTION OF THE DRAWINGS

FIG. 1 is a perspective view of a dental model with which the present invention may be used;

FIG. 2 is an exploded view, showing a portion of the dental model and the manner in which a die segment cooperates with the novel dowel pin and the base to position the die segment with respect to the base and other die segments;

FIG. 3 is a cross-sectional plan view, taken along the line 3—3 in FIG. 1;

FIG. 4 is a cross-sectional view taken along the line 4—4 in FIG. 3;

FIG. 5 is a cross-sectional view of the dowel pin, taken along the line 5—5 in FIG. 2;

FIG. 6 is an elevation view of a dowel pin in accordance with the invention; and FIG. 7 is a cross-sectional view taken along the line 7—7 in FIG. 4.

DETAILED DESCRIPTION

Referring now to the drawings in detail, wherein like reference numerals indicate like elements, there is seen in FIG. 1 a dental model designated generally by the reference numeral 10.

The model 10 consists of a base 12, typically cast from the materials known in dentistry as laboratory stone or plaster, and a die model 14, typically cast from the material known in dentistry as die stone.

Referring to FIG. 2, the die model 14, which is cast in a single piece, may be cut, by sawing or the like, into individual segments, each, like the illustrated segments 16, 18, 20 providing a die of one or more teeth. At least one dowel pin, such as the dowel pin 22 seen in FIG. 2, serves to position and index each of the segments 16, 18, 20 with respect to the base 12.

The dowel pin 22 in accordance with the invention comprises a stem 24, which, like conventional dowel pins, may have a generally cylindrical knurled stem 24. Referring to FIG. 4, in which the die segment 16 is seen in cross section, the stem 24 of the dowel pin 22 may be permanently embedded in the die segment 16 in a conventional manner, and affixed to the die segment 16 by adhesive or other suitable means, not shown. In conventional practice, the die model 14 is drilled to receive the stems 24 of the dowel pins 22 before being cut into individual segments.

Referring now to FIGS. 2 and 4, coupled to the stem 24 of the dowel pin 22 is a body portion 26. The body portion 26 extends axially from the stem 24 (and vice versa), and is axially aligned therewith. The body portion 26 is tapered, and has what may be described as a generally frusto-conical shape, tapering from an enlarged upper part adjacent to the stem 24 to a relatively narrow distal end 28.

As is perhaps best seen in FIG. 5, the body portion 26 of the dowel pin 22 is, at its upper part, generally circular in cross section, but the circular cross-section is modified by a first facet 30, which faces laterally outwardly with respect to the longitudinal axis of the body portion (as is perhaps best seen in FIG. 6). As is evident from FIG. 6, the facet 30 is disposed obliquely with respect to the axis of the body portion 26.

Referring now to FIGS. 2 and 4, the body portion 26 has on it a second facet 32, facing laterally outwardly with respect to the axis of the body portion 26, and disposed obliquely with respect to the first facet 30. The second facet 32 is also disposed somewhat obliquely to the axis of the body portion 26, but, in the presently preferred embodiment, not as markedly as the first facet 30.

A third facet 34 extends transversely with respect to the axis of the body portion 26, and faces toward the distal end 28 of the body portion 26. The third facet 34 defines a plane which intersects both the first facet 30 and the second facet 32.

The third facet 34 is disposed, in the thicker (upper) part of the body portion 26, and preferably, approximately two-thirds of the axial distance from the distal end 28.

The above-described first, second and third facets, 30, 32 and 34, provide a positive positioning and index means for the die segments 16, 18 and 20 with respect to the base 12. In this regard, it will be seen from FIGS. 2 and 4 that the dowel pin 22, when the die segment 16 is placed in association with the base 12, resides in a cavity 36. Because, as is conventional, the base 12 is molded in situ around the die model 14 and dowel pins 22, each cavity 36 conforms in its contour to the outer contour of the body portion 26 of the dowel pin 22.

The above described first, second and third facets 30, 32 and 34 provide planes, edges and angles which serve, with the taper of the body portion 26, to positively index and position each die segment with respect to the base 12. Thus, referring to FIGS. 2, 4 and 6, the first facet 30 intersects the generally circular outer contour of the body portion 26 at respective edges 38 and 40 of the kinds which would be provided by certain conventional dowel pins. In reference to FIG. 7, the intersection of the second facet 32 and the first facet 30 is defined by an edge 42, and the intersection of the second facet 32 and the outer contour of the body portion 26 is defined by yet another edge 44. It will be apparent from FIGS. 2, 4 and 7 that the contours of the cavity 36 abutting the first facet 30 and second facet 32 and the interaction of the edges 38-44 and their counterparts in the cavity 36 prevent rotation of the dowel pin 22.

The taper of the body portion 26, the third facet 34 and the tip of the distal end 28 abut corresponding and like-contoured walls of the cavity 36, and serve to positively index the height of the die segment with respect to the base 12.

The above-described configuration, it has been found, assures positive repositioning of each die segment 16, 18, 20, etc. after the die segment has been removed from the base 12 for study, handling and use in connection with the preparation of dental prothesis. The numerous planes, edges and angles of the dowel pin 22 and cavity 36 constrain movement of the dowel pin 22 (and hence the die segments 16, 18, 20, etc.) with respect to the base 12, and make models 10 which use dowel pins 22 in accordance with the present invention relatively durable. Thus, the present invention provides continued accurate seating of the die segments notwithstanding minor wear and tear on the cavity 36 occasioned by repeated handling and use of the model 10.

In this regard, it is believed that the numerous planes, edges and angles result in a reduction of the stress at any given locality in the cavity 36, thus, minimizing the tendency of the cavity to erode or become enlarged through usage. This result is achieved without the need for additional structural elements which have been used from time to time with dowel pins heretofore known, such as those illustrated in U.S. Pat. No. 4,054,995, issued Oct. 25, 1977. That patent, among others, suggests the use of sleeves, embedded in the base of the model, to receive the distal ends of a dowel pin. In the use of the present invention, molding of the base 12 is done in precisely the same manner as it would if conventional dowel pins were used. No additional parts or special techniques are needed or used.

The present invention may be embodied in other specific forms without departing from its spirit or essential attributes. Accordingly, reference should be made to the appended claims, rather than the foregoing specification and accompanying drawings, for an indication of the scope of the invention.

I claim:

1. A dowel pin for use in a dental model, comprising a stem adapted to be embedded in a die, and a body portion coupled to said stem and extending axially therefrom, said body portion being generally frusto-conical in shape and having a first facet thereon facing laterally outwardly with respect to the longitudinal axis of said body portion, a second facet on said body portion facing laterally outwardly with respect to said body portion and disposed obliquely with respect to said first facet so that said facets intersect, and a third facet on said body portion extending transversely with respect to the axis of said body portion and intersecting said first and second facets, said first facet extending for substantially the length of said body portion, and said second facet extending for more than half of the axial length of said body portion so that said third facet is disposed at a location in the upper half of said body portion and facing toward said distal end.

2. A dowel pin for use in a dental model, comprising a stem adapted to be embedded in a die, and a body portion coupled to said stem and extending axially therefrom, said body portion being generally frusto-conical in shape and having a first facet thereon facing laterally outwardly with respect to the longitudinal axis of said body portion, a second facet on said body portion facing laterally outwardly with respect to said body portion and disposed obliquely with respect to said first facet so that said facets intersect, and a third facet on said body portion extending transversely with respect to the axis of said body portion and intersecting said first and second facets, said first facet extending for substantially the length of said body portion, and said second facet extending for more than half of the axial length of said body portion, so that said third facet is disposed at approximately two-thirds of the axial dimension of said body portion from the distal end of said body portion and facing toward said distal end.

3. A dowel pin in accordance with claim 2, wherein said first facet comprises a plane oriented at an oblique angle with respect to the axis of said body portion, and said second facet comprises a planar surface oriented generally parallel to the axis of said body portion.

4. A dowel pin in accordance with claim 2, wherein said first facet comprises a plane oriented at an oblique angle with respect to the axis of said body portion and said second facet comprises a planar surface oriented generally parallel to the axis of said body portion, and said third facet comprises a planar surface oriented generally perpendicular to the axis of said body portion.

* * * * *